United States Patent [19]

Gerhart et al.

[11] Patent Number: 4,843,112

[45] Date of Patent: Jun. 27, 1989

[54] BIOERODABLE IMPLANT COMPOSITION

[75] Inventors: Tobin N. Gerhart, Brookline; Wilson C. Hayes, Lincoln, both of Mass.

[73] Assignee: The Beth Israel Hospital Association, Boston, Mass.

[21] Appl. No.: 24,973

[22] Filed: Mar. 12, 1987

[51] Int. Cl.$^4$ ............................................. C08K 3/32

[52] U.S. Cl. ............................ 523/114; 523/113; 523/115; 523/116; 524/417; 424/78; 623/16

[58] Field of Search .............. 523/113, 114, 115, 116; 524/417

[56] References Cited

U.S. PATENT DOCUMENTS

| | | | |
|---|---|---|---|
| 3,463,158 | 8/1969 | Schmitt et al. | 128/334 |
| 3,811,444 | 5/1974 | Heller et al. | 424/22 |
| 3,857,932 | 12/1974 | Shepherd et al. | 424/19 |
| 3,882,858 | 5/1975 | Klemm | 128/92 C |
| 3,920,806 | 11/1975 | Nessel et al. | 424/22 |
| 3,976,071 | 8/1976 | Sadek | 128/260 |
| 3,978,203 | 8/1976 | Wise | 128/260 |
| 3,982,537 | 9/1976 | Bucalo | 424/19 |
| 3,991,766 | 11/1976 | Schmitt et al. | 424/19 |
| 3,997,512 | 12/1976 | Casey et al. | 424/78 |
| 4,054,138 | 10/1977 | Bucalo | 128/260 |
| 4,069,307 | 1/1978 | Higuchi et al. | 424/19 |
| 4,076,798 | 2/1978 | Casey et al. | 424/22 |
| 4,080,969 | 3/1978 | Casey et al. | 128/156 |
| 4,131,597 | 12/1978 | Bluethgen et al. | 106/35 |
| 4,141,864 | 2/1979 | Rijke et al. | 524/417 |
| 4,148,871 | 4/1979 | Pitt et al. | 424/22 |
| 4,150,108 | 4/1979 | Graham | 424/22 |
| 4,181,983 | 1/1980 | Kulkarni | 128/296 |
| 4,192,021 | 3/1980 | Deibig et al. | 106/161 |
| 4,249,531 | 2/1981 | Heller et al. | 128/260 |
| 4,291,013 | 9/1981 | Wahlig et al. | 424/16 |
| 4,291,015 | 9/1981 | Keith et al. | 424/22 |
| 4,293,539 | 10/1981 | Ludwig et al. | 424/19 |
| 4,309,488 | 1/1982 | Heide et al. | 428/547 |
| 4,322,398 | 3/1982 | Reiner et al. | 128/360 |
| 4,331,652 | 5/1982 | Ludwig et al. | 424/19 |
| 4,333,919 | 6/1982 | Kleber et al. | 424/19 |
| 4,344,968 | 8/1982 | Aoda et al. | 424/22 |
| 4,346,709 | 8/1982 | Schmitt | 128/260 |
| 4,356,572 | 11/1982 | Guillemin et al. | 128/92 B |
| 4,365,357 | 12/1982 | Draenert | 128/92 C |
| 4,373,217 | 2/1983 | Draenert | 523/114 |
| 4,450,150 | 5/1984 | Sidman | 424/14 |
| 4,452,973 | 6/1984 | Casey et al. | 528/354 |
| 4,481,353 | 11/1984 | Nyilas et al. | 528/303 |
| 4,491,575 | 1/1985 | Korsatko | 424/22 |
| 4,497,075 | 2/1985 | Niwa et al. | 106/306 |
| 4,517,006 | 5/1985 | Drake et al. | 523/122 |
| 4,536,387 | 8/1985 | Sakamoto et al. | 424/14 |
| 4,539,981 | 9/1985 | Tunc | 623/16 |
| 4,550,449 | 11/1985 | Tunc | 623/16 |
| 4,563,489 | 1/1986 | Urist | 523/115 |
| 4,578,384 | 3/1986 | Hollinger | 514/8 |
| 4,581,028 | 4/1986 | Fox, Jr. et al. | 424/27 |
| 4,594,407 | 6/1986 | Nyilas et al. | 523/113 |
| 4,596,574 | 6/1986 | Urist | 623/16 |
| 4,610,692 | 9/1986 | Eitenmuller et al. | 623/16 |
| 4,620,327 | 11/1986 | Caplan et al. | 623/16 |
| 4,629,621 | 12/1986 | Snipes | 424/19 |
| 4,634,720 | 1/1987 | Dorman et al. | 524/417 |
| 4,636,526 | 1/1987 | Dorman et al. | 524/417 |
| 4,661,536 | 4/1987 | Dorman et al. | 523/114 |
| 4,698,375 | 10/1987 | Dorman et al. | 524/417 |
| 4,722,948 | 2/1988 | Sanderson | 523/113 |

FOREIGN PATENT DOCUMENTS 2156824 11/1986 United Kingdom .

OTHER PUBLICATIONS

J. Vainio, *Arch, Orthop. Traumat. Surg.*, 92, 169-174 (1978).

A. C. Ibay et al., *Polymer Materials Science and Engineering*, 53, 505-509 (1985).

B. Roed-Peterson, *Int. J. Oral Surg.*, 3, 133-136 (1974).

*Primary Examiner*—Lewis T. Jacobs
*Assistant Examiner*—David W. Woodward

[57] ABSTRACT

An improved bone cement is comprised of a particulate biocompatible calcium phosphate ceramic and particulate resorbable calcium salt dispersed in a cross-linked biodegradable polyester matrix. The polymer/salt-particle composite exhibits good biomechanical strength/modulus characteristics with surgically acceptable cure times. When used for sustained release of biologically active agents in a physiological environment, controlled release of biological agents that are mixed into the composite can be achieved as the cement biodegrades. When used for bone/implant fixation, or as a filler or cement for bone repair, gradual biodegradation of the cement composite permits, under suitable circumstances, eventual replacement of the cement with developing bone tissue.

16 Claims, 3 Drawing Sheets

BIOERODABLE IMPLANT COMPOSITION

BACKGROUND AND SUMMARY OF THE INVENTION

This invention relates to an implantable bioerodable composition useful for the repair of living bone and for the administration of biologically active substances. More particularly, this invention relates to a moldable, biocompatible, polyester/particulate composite that can be used for reinforcement of fractures and defects in bone, for fixation of implants and prostheses in bone, and for controlled-release delivery of biologically active agents.

Applicants have found that incorporation of biocompatible calcium phosphate ceramics and resorbable calcium salts into a cross-linked biodegradable polyester matrix produces a cement-like composition having the combined features of developing excellent biomechanical strength within a short cure time and the capacity to degrade progressively, in vivo, permitting, under suitable conditions, eventual replacement of the cement by body tissue. Thus, for example, where the present bioerodable composition is implanted in contact with bone for use to repair skeletal deformities and injuries, to treat infections and diseases, or to "fix" prosthetic appliances in bone, the composition is gradually resorbed and may then be replaced with living bone.

Surgical cements are well known in the art. Such cements are commonly used for implant fixation in the surgical replacement of joint and bone tissue with prosthetic appliances. At the time of surgery the cement, in a fluid or semi-fluid pre-cured form, is injected or otherwise applied between the bone and implant, flowing around the contours of the bone and implant and into the interstices of cancellous bone. Upon hardening (curing), the cement mechanically-interlocks the bone and implant.

Poly(methyl methacrylate) (PMMA) is the most widely used bone cement. PMMA cement comprises two components, a powder of prepolymerized methyl methacrylate and a liquid monomer, methyl methacrylate, that are mixed at the time of surgery to form a paste-like cement material. PMMA cement is "permanent" in the sense that it is not degraded within the body. However, PMMA does not always provide "permanent" implant fixation. Loosening of prosthetic appliances due to cement failure has long been recognized as the single most prevalent problem in conventional prosthetic arthroplasty, placing a serious limitation on the successful duration of joint and bone replacement surgery. PMMA cement can sustain fatigue damage and has been known to crack and fail due to biomechanical overstressing. Yet another problem encountered with the current PMMA bone cement is that of the resorption of bony tissue immediately adjacent to the bone cement associated with the formation of a biologically active fibrous tissue membrane. Inducement of the formation of this membrane, which contains bone resorbing cells and enzymes, may be a second mechanism, in addition to biomechanical overstressing, whereby PMMA cement loses its purchase in the surrounding bone and thereby fails to provide secure implant fixation.

More recent research efforts concerning fixation of bone prostheses have been directed to development of bone cements that are more compatible with bone tissue and to definition of implant surfaces capable of receiving direct bone ingrowth to enhance the bone-implant interlock. For example, prosthetic appliances have been constructed with a highly porous coating on their bone-contacting surfaces, providing interstices into which bone tissue can grow to effect direct bone fixation of the implant. For a bone to interlock with the porous surface structure of the implant, however, the implant must be firmly fixed at the time of surgery and load application must be minimized during the ingrowth period. This fixation method is, therefore, not entirely satisfactory because it is very difficult to provide adequate immobilization and stabilization of the implants during the bone ingrowth process. Further it is impossible to achieve bone ingrowth if a sufficiently large gap exists between the patient's bone and the porous implant surface.

One embodiment of the present invention relates to the use of a cross-linked biodegradable polyester/particulate composite for surgical bone repair and implant fixation. The invention is based on the discovery that particles of biocompatible sintered calcium phosphate ceramics and more porous and resorbable calcium salts can be incorporated into a cross-linked biodegradable polymer matrix to produce a surgical cement possessing physical and biological properties that are superior to conventional fixation cements. The polymer matrix is a biodegradable polyester solidified, or cured, immediately following placement in vivo by reaction with a chemical cross-linking agent. The polymer matrix serves as a supporting binder for particles of biocompatible inorganic salts and ceramics. The cured cement exhibits excellent biomechanical properties within short cure times. A patient receiving an implant fixed using the present cross-linked polyester composite as a cement could be ambulatory early after surgery, thereby facilitating rapid rehabilitation and minimizing costly hospitalization.

The polyester composite of this invention is formulated to allow a unique multi-stage process in which the cement is gradually resorbed and could be replaced in vivo under suitable conditions by growing natural bone. Thus an implant originally secured using the present cement could, with time, be secured by direct contact with living bone. Initially, particulate calcium salts in the cement are eluted from the polyester matrix by body fluids creating small voids or cavities in the polymer matrix. Over time, the more slowly resorbable particulate ceramic component is wholly or partially resorbed, and the polyester matrix itself degrades in vivo into its component non-toxic assimilable dicarboxylic acids, and dihydric or polyhydric alcohols. As the matrix of the cement slowly degrades voids are formed which can be filled in by new bone. Eventually the extent of the new bone ingrowth could contact and secure the prosthetic appliance. The extent of new bone ingrowth will vary depending upon local conditions affecting the implant. For instance, new bone ingrowth can be expected only if the bone cement is implanted intraosseously as opposed to subcutaneously or intramuscularly. Furthermore, cancellous bone, with its greater blood supply, is more likely to facilitate bone ingrowth than cortical bone. The presence of an infecting organism would have an adverse affect on ingrowth. Proportionally less ingrowth will occur with a large amount of implanted cement. Mixing host bone into the cement before use could facilitate bulk regrowth and new bone ingrowth.

In contrast to the situation mentioned above where a PMMA-fixed prosthesis can work loose with formation of surrounding fibrous tissue, living bone is able to heal and to remodel itself in response to stress; it is, therefore, resistant to the problem of failure with repeated loading. This invention represents a significant improvement in bone implant methodology.

It is known in the bone cement art to combine a bioresorbable particulate compound such as tricalcium phosphate with a non-biodegradable polymeric resin. See, for example, U.S. Pat. No. 4,373,217; U.K. Application No. 2,156,824; J. Vanio, Arch. Orthop. Traumat. Surg., 92, 169-174 (1978). However, such compositions do not function in vivo as does the cement of this invention. Because polymer resins of prior art composites are not biodegradable, prior art composite cements cannot be replaced by growing bone tissue.

The use of biodegradable polymers in vivo is also known in the art. Biodegradable polymers have been described for a variety of applications, including controlled release dosage forms and bioresorbable sutures. See U.S. Pat. Nos. 3,463,158; 4,080,969; 3,997,512; 4,181,983; 4,481,353; and 4,452,973. Ibay et al. describe the preparation and use of moldable implant appliances from vinylpyrrolidone cross-linked poly(propylene glycol fumarate) (PPF) for use as temporary replacements for soft tissue and/or bone following trauma. A. C. Ibay et al., *Polymer Material Science and Engineering*, 53, 505-509 (1985). Absorbable polyglycolic acid suture has been used successfully for internal fixation of fractures. B. Roed-Peterson, *Int. J. Oral Surg.*, 3, pp. 133-136 (1974). There is nothing, however, to suggest use of cross-linked biodegradable polymer composites for implant fixation. Nor is there any suggestion to combine biodegradable cross-linkable polyesters with biocompatible particulate calcium salts and ceramics to form the present particulate/polymer composites finding use as bone cements and as effective delivery systems for the sustained-release of biologically active substances.

It is therefore, an object of this invention to provide a biocompatible resorbable surgical cement for repairing living bone.

It is another object of this invention to provide a method for permitting bone ingrowth and bone adhesion to implanted prostheses.

Another object of this invention is to provide a biodegradable implantable composite comprising a cross-linked biodegradable organic polymer in combination with particulate, biocompatible calcium phosphate ceramics and a resorbable calcium salts.

Still a further object of this invention is the use of particulate/cross-linked polyester composites as means for sustained-release delivery of drugs for treatment of disease in warm-blooded vertebrates, and drug depot devices utilizing said composites.

DETAILED DESCRIPTION OF THE INVENTION

Figure 1:
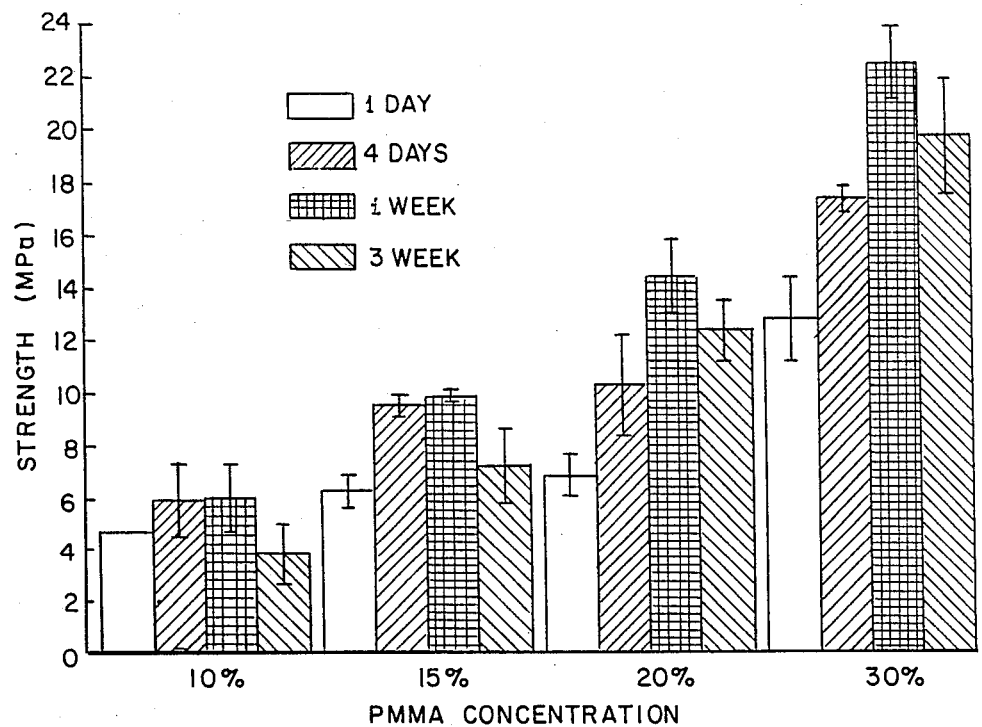
FIG. 1 illustrates compressive strength values measured in Megapascals for various weight compositions of PPF/MMA cement prepared in accordance with this invention, implanted as 6×12 mm cylindrical specimens subcutaneously in rabbits, and measured at time intervals ranging from one day to three weeks after implantation.

The present invention is directed to a biodegradable cement composition adapted for use in the surgical repair of living bone and for the controlled-release delivery of pharmaceutical agents. The composition comprises a particulate biocompatible calcium phosphate ceramic and a resorbable calcium salt dispersed in a cross-linked biodegradable polyester matrix. The composition can be applied to bone-contacting surfaces of prosthetic appliances (as a cement), or it can be inserted into and around bone defects and cavities (as a filler), thereby providing an effective means for treating or repairing living bone. When a pharmaceutical agent is incorporated into the cross-linked biodegradable matrix it serves as a depot device for controlled-release of the pharmaceutical agent. Release of the agent occurs over a prolonged period of time upon implantation.

In general, the invention features a biodegradable polyester in combination with particulate calcium phosphate ceramics and resorbable calcium salts. Polyesters useful in this invention are non-toxic, biodegradable, and bioresorbable, i.e., their degradation products are used by or are otherwise eliminated from the human body via existing biochemical pathways. The polyesters should also be chemically cross-linkable, i.e., possess functional groups which will allow the polyester polymer chains to be reacted with cross-linking agents reactive with said functional groups. Suitable polyester materials include polyesters formed from biocompatible di- and tri-carboxylic acids or their ester-forming derivatives (e.g., acid chlorides or anhydrides) and di- or polyhydric $C_2$-$C_6$ alcohols. The functional groups in the polyester allowing for polyester cross-linking can derive from either the alcohol or the acid monomer components of the polyester.

Representative carboxylic acids for formation of polyesters useful in this invention include Kreb's cycle intermediates such as citric, isocitric, cis-aconitic, alpha-ketoglutaric, succinic, malic, oxaloacetic and fumaric acid. Many of such carboxylic acids have additional functionalities which can allow cross-linking and therefore means for curing the present cement formulation from a paste-like moldable mass to a hardened cement state. Fumaric acid is a preferred acid for forming the polyester of the present invention. It is a dicarboxylic acid having a free-radical reactive double bond well suited for free radical induced cross-linking reactions.

Illustrative of $C_2$-$C_6$ alkyl or aklylene alcohols useful to form plyesters in accordance with this invention are ethylene glycol, 2-buten-1,4-diol, 2-methyl-2-buten-1,4-diol, 1,3-propylene glycol, 1,2-propylene glycol, glycerine, 1,3-butanediol, 1,2-butanediol, 4-methyl-1,2-butanediol, 2-methyl-1,3-propanediol, 4-methyl-1,2-pentanediol, cyclohexen-3,4-diol and the like. In a preferred embodiment the polyester component of the present composite cement is poly(propylene glycol fumarate)(PPF) formed by the condensation (esterification) reaction of propylene glycol and fumaric acid.

PPF is advantageous in the present invention because PPF possesses two chemical properties that are critical to the function of a biodegradable bone cement. The first is the ease by which PPF can be degraded in vivo into its original fumaric acid and propylene glycol subunits. Both fumaric acid and propylene glycol are non-toxic and well-tolerated in vivo. As a Kreb's cycle intermediate, fumaric acid plays an essential role in the process by which food is converted into energy. Propylene glycol is used throughout the food industry as a food additive and can be metabolized or excreted by the body. The second critical property is that each subunit of the PPF prepolymer contains an activated unsaturated site through which the polyester can be cross-linked with various olefinic free-radical induced cross-linking agents.

The polyester is cross-linked during the curing period for the present composite cement to form a solidified cement matrix. Where the reactive chemically functional groups in the polyester are carbon-carbon double bonds (e.g., in the preferred PPF polyester component) representative cross-linking agents are methyl methacrylate (MMA), N-vinylpyrrolidone, and like olefinic cross-linking agents. A preferred cross-linking agent is MMA, which exists as a clear liquid at room temperature. It is particularly suitable for free radical induced cross-linking of PPF in accordance with a preferred embodiment of this invention.

The preparation of the present composite cement typically involves combining the polyester and the cross-linking agent into a substantially homogeneous mixture, and adding the particulate calcium phosphate ceramic and calcium salt to form a moldable composite cement mass which hardens on curing, i.e., completion of the cross-linking reaction. The number average molecular weight [M(n)] and molecular weight distribution [MWD] of the polyester should be such that the polyester and cross-linking agent can be combined to form a substantially homogeneous mixture. Preferably the cross-linking agent is a liquid and the polyester is substantially soluble in, or miscible with, the cross-linking agent. Alternatively, the cross-linking agent can be a solid soluble in a liquid low molecular weight polyester, or a liquid miscible therewith. Under ideal circumstances, the cross-linking reaction will result in a homogeneous (uniformly cross-linked) polyester/particulate composite cement.

In a Preferred embodiment poly(propylene glycol fumarate)(PPF) is combined with an amount of methyl methacrylate sufficient upon reaction initiation, to cross-link the polyester to the level necessary to form a rigid cross-linked PPF polymer matrix for the admixed particulate calcium salts. Preferred MWD for the PPF ranges from about 500 to about 1200 M(n) and from about 1500 to about 4200 M(w).

In a preferred embodiment of this invention, the liquid polymer phase of the cement formulation is about 80 to about 95 percent by weight PPF and about 5 to about 20 Percent by weight MMA monomer. The optimal weight percentages for mechanical strength are approximately 85 percent PPF and about 15 percent MMA. The MMA monomer is typically stabilized to prevent premature Polymerization, i.e., prior to mixing with PPF, with a few parts per million of hydroquinone.

It is important that the proportions of PPF and MMA are controlled. If too much MMA monomer is added, the MMA molecules can polymerize themselves without being interrupted by the PPF chains. The result is a material that behaves like conventional PMMA bone cement and does not biodegrade. If too little MMA monomer is added, the PPF polymer chains will not be effectively cross-linked and the cement will not cure to form a matrix of sufficient rigidity.

The MMA-PPF cross-linking reaction proceeds via a free-radical propagated polymerization reaction. The cross-linking reaction therefore is, in practice, accelerated by addition of a free-radical initiator. One suitable free-radical initiator for this process is benzoyl peroxide.

A catalytic amount (less than 1% by weight) of dimethyltoluidene (DMT) is typically added to accelerate the formation of free radicals at room temperature. Thus, the rate of cross-linking (i.e. time for curing or hardening of the cement) can be adjusted by controlling the amount of DMT added to the PPF/MMA mixture. The cement-curing rate can be adjusted so that the cement is substantially cured in a period ranging from less than a minute to over 24 hours. The preferred curing time depends, of course, upon what is the most practical period of time for surgical purposes. The curing period should be sufficiently long to allow the surgeon time to work with the cement to mold it or apply it to the appropriate surfaces. At the same time, the cure rate should be high enough to effect, for example, implant stabilization within a short time following the surgical procedure. The polymerization or solidification period for bone implant fixation typically ranges from about 5 to about 20 minutes, and preferably about 10 minutes.

The particulate phase of the present cement is comprised of biocompatible particulate calcium phosphate ceramics and particulate bioresorbable calcium salts. The particulate phase initially acts as a strength-imparting filler, much like the aggregate component of concrete. However, in vivo, the calcium salt particles are slowly eluted from the cement matrix by body fluids, leaving sites for bone ingrowth into the polymer matrix. Exemplary resorbable calcium salts effective in the composition of this invention include calcium sulfate, calcium sulfate hemihydrate (plaster of Paris), calcium carbonate, calcium hydrogen phosphate, certain porous precipitated forms of calcium phosphate and the like.

Biocompatible calcium phosphate ceramics are selected particularly in the bone repair embodiment of this invention for their known properties vis a vis growing/living bone; that is, they are known to promote interfacial osteoconduction. Osteoconduction refers to the ability of a substance to induce bone to grow on it. As used herein the term "calcium phosphate ceramics" is to be distinguished from the second particulate component "bioresorbable calcium salts", and refers to a number of sintered (heat-consolidated) materials approximately defined by the formula $Ca_3(PO_4)_2$ including not only tricalcium phosphate itself but also apatites, such as hydroxyapatite, and phosporites. The particulate calcium phosphate ceramics used in accordance with this invention are characterized themselves as "resorbable" but they are resorbable at a much lower rate than the more porous particulate "calcium salts" component of the present composites. Calcium phosphate ceramics are in general prepared by sintering more soluble calcium salts, for example, $Ca(OH)_2$, $CaCO_3$ and $CaHPO_4$ with $P_2O_5$ or with each other. Calcium phosphate ceramics and their use in implant materials are known in the art. See, for example, U.S. Pat. Nos. 3,787,900; 4,195,366; 4,322,398; 4,373,217 and 4,330,514.

Bone particles, either autograft or allograft, can also b included in the particulate phase. Including natural bone in the cement enhances the property of osteoinduction or the ability to induce new bone formation.

In a preferred embodiment of this invention, a mixture of calcium salts and calcium phosphate ceramics is used to form the particulate phase. A coarse tricalcium phosphate ceramic having a porous surface and a particle diameter of about 300 to about 600 microns is mixed with fine-particulate or powdered calcium carbonate or plaster of paris (calcium sulfate hemihydrate) having a maximum particle size of less than about 10 microns and preferably less than about 5 microns in diameter. Use of smaller diameter tricalcium phosphate particulate lowers the mechanical strength of the cement but increases its ability to penetrate into small interstices. The particulate tricalcium phosphate is preferably combined with the calcium carbonate or calcium sulfate in ratios ranging from about 1:4 to about 4:1 by weight, and preferably in a ratio of about 1:1 to form the particulate component of the present biodegradable polymer composites.

In the cement composition of this invention, the weight ratio of calcium salts and calcium phosphate ceramics (the particulate phase) to the polyester matrix phase (polyester plus cross-linking agent) can range from about 5:1 to about 1:2. Preferably, the cement composition is prepared by mixing about 2 parts by weight of particulate phase with about 1 part by weight polymer matrix phase. The ratio of particulate phase to polymer phase can be adjusted to provide the functional characteristics warranted by any given surgical application of the composite cement.

A kit for preparing the particulate cross-linked polyester composite of this invention can be conveniently packaged for surgical applications. For example, the inorganic particulate calcium salts, calcium phosphate ceramics, and benzoyl peroxide can be packaged as a particulate powder phase while the PPF and MMA can be packaged as a liquid phase.

In the operating room, the surgeon mixes the powder and liquid (polymer plus cross-linker) phases to form a paste-like mass. In a preferred composition, the resulting surgical cement is comprised of approximately one-third by weight of the liquid phase and approximately two thirds by weight of the particulate phase. At this time, the surgeon may wish to add to the cement mixture bone that is taken from the patient and ground into Particulate form in order to enhance osteoinduction or the ability to induce new bone formation to the cement. The cross-linking/curing process begins immediately at room temperature when the DMT is added. Alternatively all ingredients can be mixed together except for the benzoyl peroxide which is added when initiation of the curing process is desired. The cross-linking reaction can transform the bone cement from an injectable or moldable paste into a durable solid particulate composite within about 10 minutes.

Although cement solidification can proceed sufficiently within a 10 minute period to form a solid material, the reaction continues to proceed at a slower rate for a period of several hours to several days.

The particulate calcium salts and organic polymers employed in the composition of the present invention are available commercially or are readily prepared through procedures which are known in the art.

The present particulate/polymer composites have been found to provide an excellent matrix for the sustained release in vivo of biologically active substances incorporated into the composite prior to or during the cross-linking (curing) step for preparing the present composites. Thus a drug substance/pharmaceutical agent incorporated into the pre-crosslinked polymer/particulate mixture to form about 0.1 to about 33% by weight, more preferably about 2% to about 5% by weight, of the drug-composite mixture will be released in vivo (upon implantation of the cured composite) over a period ranging from about two days to about 30 days and longer depending on the nature of the composite formulation.

Release rate from a delivery system based on the present composites is a function of the degree of cross-linking, the nature and concentration of the drug substance in the matrix, particulate size/solubility, nature/biodegradability of polyester component and the "in vivo environment" of the implanted composite. Thus use of the present composites as a drug delivery system allows for a significant degree of control over drug release.

The cross-linking reaction employed to "cure" the present composites is only mildly exothermic compared to, for example, PMMA polymerization. This allows for formulation of sustained release delivery systems for more thermally labile drugs.

The drug delivery systems in accordance with this invention can be formulated and implanted, or injected, either before or after curing (the cross-linking reaction) is complete. The drug/cross-linked polymer/particulate composites are typically implanted surgically at a site in the body where high drug concentrations are desired. Thus, for example, in the treatment of osteomyelitis, antibiotic-containing composites can be molded to conform to naturally occurring bone defects or they can be inserted into cavities formed by the surgeon specifically for receiving the composition. Similarly, the composites can be implanted or injected into soft tissue for sustained drug release. An important advantage of the present composite delivery systems is that a second surgical procedure to remove the "spent" drug delivery device is not required. The device is with time degraded and its degradation products are absorbed by the body.

The present invention is further illustrated by the following examples, none of which are to be construed as limiting the invention in any respect:

EXAMPLE 1

A poly(propylene glycol fumarate) (PPF) based particulate composite surgical cement was prepared as follows: 3.0 moles of fumaric acid (348 grams) and 3.3 moles of propylene glycol (251 grams) were placed in a triple-necked 1000 cc flask with overhead mechanical stirrer, thermometer, and Barret trap beneath a condenser. The reaction was initiated by heating at 145° C. with continuous stirring. After about 2 hours, water began to collect in the Barret trap. The mixture was heated for 5 hours by which time about 40 ml of water had been collected. The temperature was then increased to 180° C. in order to drive off the propylene glycol. The progress of the reaction was monitored by removing samples and measuring their viscosity at 100° C. The viscosity initially measured about 2 poise at 100° C. and gradually rose to 15 poise, at which time the reaction was terminated. Terminating the polymerization at the proper time is critical. The proper endpoint occurs when the PPF reaches a viscosity of about 10 to about 15 poise measured at 100° C. This yields PPF with a number average molecular weight of about 500 to about 1000, preferred for use in accordance with this invention.

The mixture was cooled to room temperature to prevent further polymerization. In order to remove the excess fumaric acid precipitate, 85 parts by weight of the mixture were diluted with 15 parts by weight methylmethacrylate (MMA) monomer, placed on a rotary stirring rack for 12 hours at 37 C to assure thorough mixing, and centrifuged at 6000 RPM for 30 minutes. The PPF polymer formed the supernatant.

Six grams of the liquid 85% PPF/15% MMA mixture were mixed with the following particulate components: 0.4 grams of benzoyl peroxide powder, 7.5 grams of particulate tricalcium phosphate (30–45 mesh), and 7.5 grams of powdered calcium carbonate. These ingredients were warmed to 40°–50° C. to facilitate the mixing process. This mixture exhibited no signs of solidifying. At time of use, 2 drops of dimethyl-p-toluidine (DMT) was added and thoroughly mixed. The resulting cement was immediately molded into specimens and allowed to cure at 37 C and 100% relative humidity. The fresh cement was also implanted into experimental animals. Approximately 5 minutes working time was available before the cement began to harden. Unconfined mechanical testing of the cured molded specimens, according to ASTM standards for acrylic cements, gave a compressive strength of 19 MPa and an elastic modulus of 200 MPa.

EXAMPLE 2

In vitro tests of biodegradable cement materials prepared in accordance with Example 1 were conducted in various liquids. PPF/MMA specimens were placed in water buffered at neutral pH. Initially, the water caused slight swelling of the matrix and the specimens decreased in mechanical strength and stiffness. After a few days, with the onset of the secondary calcium ion reactions, the specimens returned to their original material properties. No evidence of degradation occurred.

Samples were also placed in an alkaline solution of pH 10. The specimens lost strength quickly because of the swelling of the polymer. Because of the polymer degradation due to the high pH, the samples did not regain strength. Within a few days, the specimens could be easily crushed with the end of a pencil.

These results were obtained for PPF/MMA specimens prepared having a weight ratio of PPF to MMA of about 85:15. When higher amounts of MMA were used, e.g., 30 weight percent, degradation of the PPF/MMA specimens did not occur. The specimens regained their material properties and maintained them indefinitely.

When the specimens were placed in an acidic solution, the plaster of Paris was quickly leached out of the specimens. The specimens lost their stiffness but retained their shape due to the strength of the polymer.

These in vitro results demonstrated that the PPF/MMA bone cement possessed appropriate mechanical properties and chemical properties for use as a biodegradable cement for orthopedic applications.

EXAMPLE 3

Additional experiments were conducted to evaluate the mechanical properties of the PPF/MMA cement in animal implantation applications. Specimens were prepared in accordance with the procedures set forth in Example 1.

Figure 2:
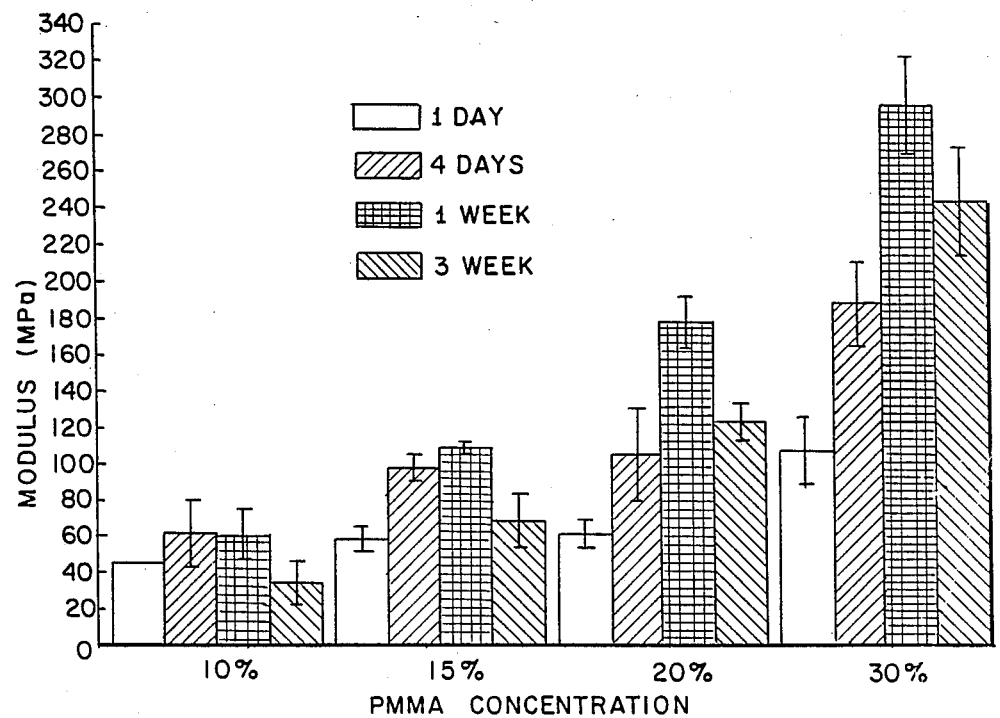
FIG. 2 illustrates elastic moduli values measured in Megapascals for various weight compositions of PPF/MMA cement prepared in accordance with this invention.
Figure 3:
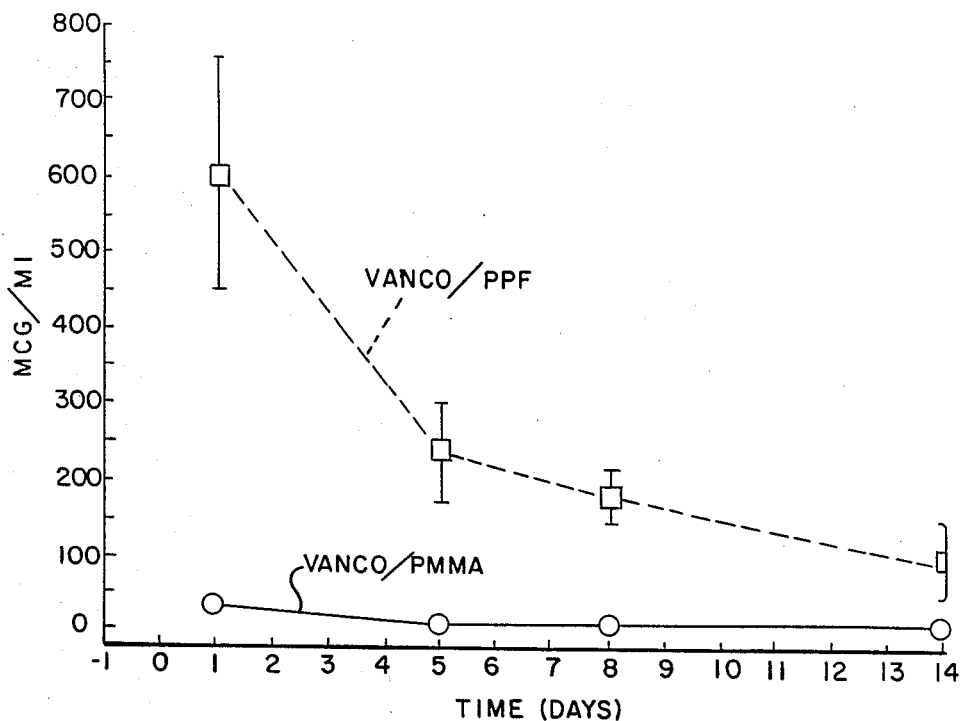
FIG. 3 is a graphic comparison of vancomycin levels in wound fluid following implantation of PMMA and PPF matrices.
Figure 4:
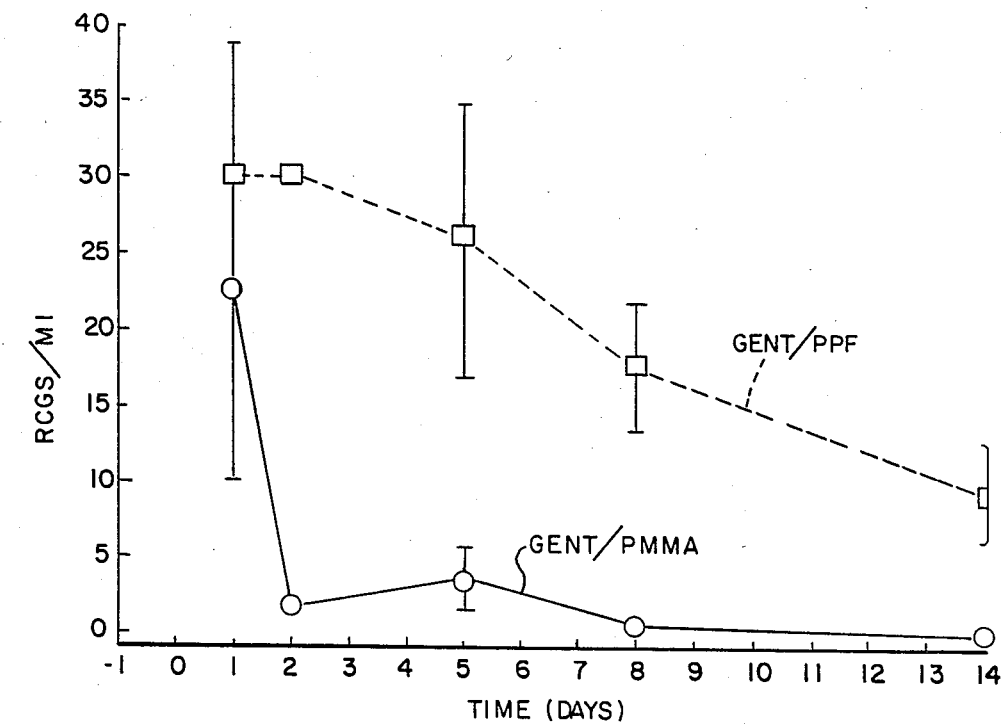
FIG. 4 is similar to FIG. 3 illustrating gentamicin levels.
Figure 5:
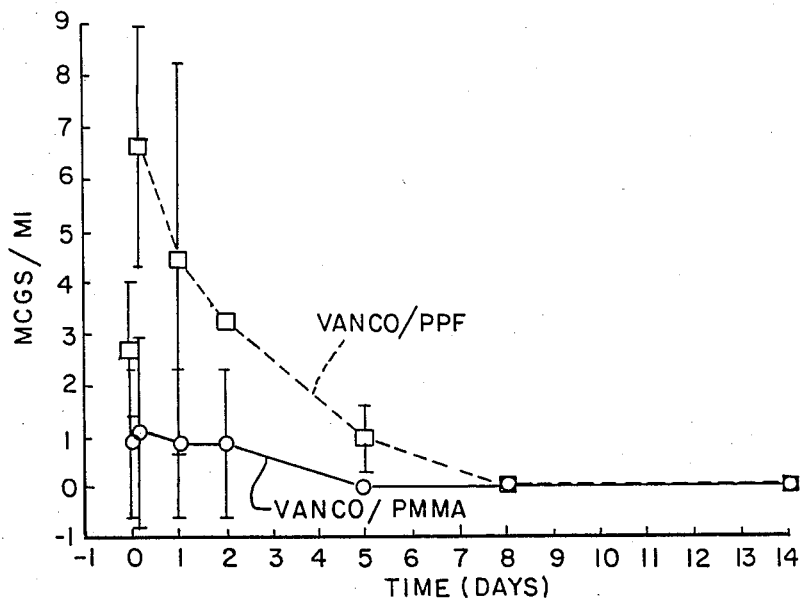
FIG. 5 is similar to FIG. 3 illustrating vancomycin levels in serum.
Figure 6:
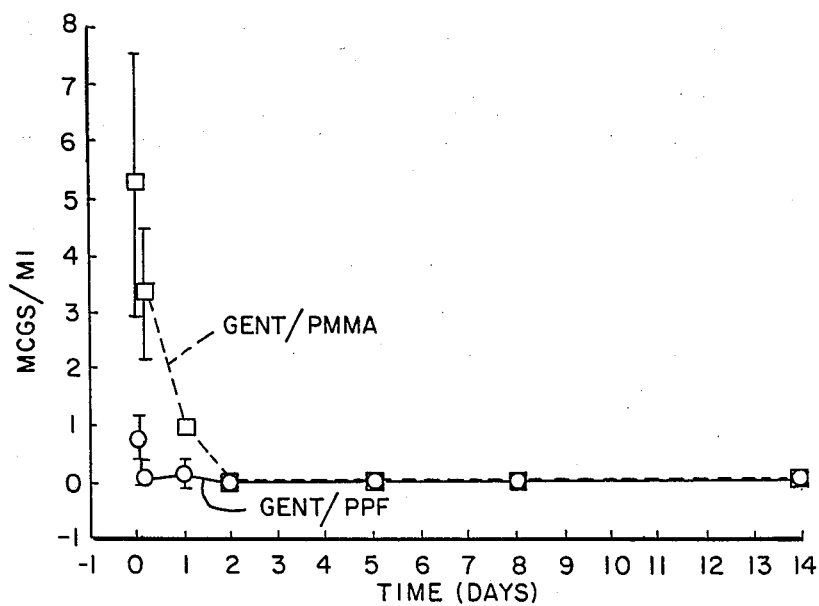
FIG. 6 is similar to FIG. 3 illustrating gentamicin levels in serum.

Three groups of standard 6×12 mm cylindrical specimens were implanted subcutaneously into a rabbit's back. At least six (6) rabbits were sacrificed for mechanical testing of implanted specimens at intervals of one day to three weeks. Results of the biomechanical evaluation are set forth in FIGS. 1 and 2. The compressive strengths of the PPF cement implant measured at one day, four days, one week, and three weeks are set forth in FIG. 1. FIG. 2 depicts the elastic moduli values measured at the same intervals.

Four different compositions of cement were tested in each rabbit. Crosslinked PPF specimens cross-linked with 10%, 15%, 20%, and 30% MMA exhibited proportionately increasing mechanical strength and modulus values. The one-day values for material properties for all concentrations were approximately one-half that of the controls. This is believed to have been caused by swelling of the polymer in a wet environment. By four days, all specimens had significantly increased their material properties. The 15% MMA specimens exhibited compressive strength of 10 MPa. This is believed to be due to the secondary calcium ion effect.

At one, two, and three week intervals, differences in material properties were observed, depending upon the MMA concentration. For 20% and 30% MMA specimens, only a slight drop in mechanical strength was noted. This is believed to have been due to the leaching out of the plaster of Paris. For the 10% and 15% MMA specimens, a more significant drop in mechanical strength was noted. This is believed to have been due not only to the plaster of Paris leaching out but also to the initial stages of polymer degradation. Subsequent experiments using 15/85 MMA/PPF cement showed that, after seven weeks of subcutaneous implantation, the compression strength of specimens had fallen below 1.0 MPa and many had crumbled and fragmented.

EXAMPLE 4

In vitro implantation of the biodegradable cement materials, prepared in accordance with Example 1, were conducted to test their effectiveness as carriers for sustained release of antibiotics. Prior to the addition of DMT, either gentamicin or vancomycin were mixed into the cement at a ratio of 1 gram of antibiotic to 30 grams of cement. The cement was then activated with DMT and molded into 6×12 mm cylindrical specimens as described above. Similar specimens were prepared with conventional PMMA cement loaded with antibiotics in the same manner. All specimens were implanted subcutaneously in rats. Wound fluids aspirated from around the implants and blood samples were measured for concentrations of antibiotics by immunoassay from 1 to 14 days post-operatively as shown in FIGS. 3, 4, 5, and 6. The PPF/MMA cement produced significantly higher local antibiotic levels in the wound fluid for both gentamicin and vancomycin, for a longer duration than did PMMA. Blood concentrations of both antibiotics remained well below toxic concentrations for both cements.

EXAMPLE 5

Treatment of Experimental Osteomyelitis in a Rat Model:

Seven Sprague-Dawley retired male breeder albino rats were divided into 4 groups as noted below. All rats underwent sterile surgical procedures under sodium pentobarbitol general anesthesia. Three successive surgical procedures were performed on each rat.

The first procedure was identical for all rats. The flat surface of the anteromedial tibial metaphysis was surgically exposed via a 1.5 cm linear incision just distal to the knee joint and 2 mm medial to the anterior tibial crest. The periosteum was split and gently moved aside using a periosteal elevator. Using a high speed drill, (Hall Air Surgery Instruments micro drill, 5053-01, Zimmer, USA) and a 2 mm burr bit, a hole was made through the anteromedial metaphyseal cortex and underlying. Care was taken not to violate the far cortex while drilling. Immediately following drilling, a suspension of S. aureus ($1.0 \times 10^6$ CFU/1 ul) was prepared using the Prompt Inoculation System (3M, No. 6306). Ten ul were injected into the wound site. This represented an inoculum of approximately $1.0 \times 10^6$ CFU. Care was taken to deliver all of the inoculum to the drill hole and avoid overflow. Immediately following inoculation, a $2 \times 3$ mm performed PMMA cylinder with a central 4 mm wire (to aid radiographic detection and facilitate later removal) was placed as a foreign body in the burr hole over the inoculum. A synthetic resorbable suture (6.0 VICRYL suture, Ethicon, Inc.) was used to partially close the periosteum over the drill hole to secure the implant. The distal $\frac{2}{3}$ of the skin incision was then closed using 4.0 VICRYL, leaving the proximal $\frac{1}{3}$ of the incision open as a potential site for drainage. Only 3 interrupted sutures were used. Postoperative lateral radiographs were obtained of all rat tibiae. Rats were then returned to cage activity for 3 weeks.

At 3 weeks, all rats except one (LONG) had their implants removed surgically using sterile technique. The appearance of the infection site was recorded. The LONG rat was left at cage activity with his original implant for the duration of the experiment. Implants were inoculated on blood agar plates and into thioglycollate broth and incubated for 24 hours at 35° C. in 5% $C)_2$. Subcultures of the broth were made as necessary to identify all infecting organisms. A sterile gauze $4 \times 4$ was used to manually wipe away pus from the drill hole and surrounding soft tissue of the left hindlimb but no formal debridement was performed. The right hindlimb underwent formula debridement of infected and necrotic bone and soft tissue bone and soft tissue and the original drill hole was reamed to 4 mm and the edges undermined using the Hlal micro air drill and 2 mm burr. Two animals were treated bilaterally with gentamicin and vancomycin and PPF/MMA packed into, and allowed to polymerize in the drill hole osteomyelitic site. Two animals were treated similarly but with gentamicin and vancomycin in PMMA. Gentamicin and vancomycin were added at a ratio of 2 gm to 60 gm of either PPF/MMA or PMMA to prepare treatment samples.

Antibiotic impregnated PPF/MMA specimens were prepared in the following manner: PPF 96 gm, of as yet unpurified fumaric acid) and MMA (1 gm) were thoroughly mixed at 37 degrees C until the PPF was completely dissolved in the MMA. The resultant matrix material (85% PPF and 15% MMA) was centrifuged at 6000 rpm for 45 minutes to remove the suspended fumaric acid. The purified PPF/MMA matric was then mixed with benzoyl peroxide (0.25 gm, a crosslinking catalyst) and the particulate phase which consisted of TCP (7.5 gm, 30-45 mesh, 355-600 micron diameter) and medical grade calcium carbonate powder (7.5 gm.). After thorough mixing of the particulate composite, gentamicin sulfate powder (Sigma Chemical Co.) or vancomycin hydrochloride lypholized powder (Lederle Parenterals Inc.) was added and mixed well. Finally, dimethyl-p-toluidine (DMT)(2 drops) was added to initiate cross-linkage of the cement. (A 22.25 gm batch of the particulate composite was prepared and 15 gms of this was mixed with 0.5 gm of antibiotic to give a 2 gm/60 gm ratio or 3.3% antibiotic. Two control animals had their initial foreign body implants removed and were not treated. All wounds were closed loosely using 2 to 3 interrupted 4.0 VICRYL sutures in the distal $\frac{2}{3}$ of the wound only. Again the proximal $\frac{1}{3}$ of each wound was left open. Pre and postoperative radiographs were obtained to document osteomyelitic changes.

Three weeks later (6 weeks post infection) all animals were sacrificed by intraperitoneal sodium pentobarbitol followed with an intracardiac injection of sodium pentobarbitol. In the operating room under sterile conditions, the hindlimbs were dismembered and partially surface sterilized by immersion in 95% alcohol followed by spraying with povidine-iodine solution which was allowed to air dry. Using a new set of sterile instruments the tibial infection site was exposed and its appearance recorded. The cement plugs and adjacent bone were then examined bacteriologically. Standardized 4mm thick 'wafer-shaped' tibia segments, which included, the infection site and cement-antibiotic plug, were cultured quantitatively. Bone segments were inoculated into 2 ml of trypticase soy broth (TSB). The mixture was vortexed, and serial 10-fold diulations in TSB were made. A 10 ul inoculum was subcultured to 5% sheep blood agar plates that were incubated for 24 hours at 35° in 5% $Co_2$. Colonies were counted on plates with approximately 30-100 colonies only.

Results: Three weeks post administration of the S. aureus inoculum all animals demonstrated clinical and radiographic signs consistent with established chronic osteomyelitis. These included abscesses, draining sinuses, radiographic osteolysis and sequestration, periosteal new bone formation and pathologic fractures. Six weeks following infection, i.e., following three weeks of treatment or control protocols, all control animals demonstrated clinical signs of infection whereas both treated groups appeared more normal clinically. Radiographs were essentially unchanged. All tibia sites from all animals grew mixed bacterial flora including S. aureus. consistent with chronic osteomyelitis. In all cases there were dramatic differences between treated animals (PPF/MMA and PMMA with antibiotics) and control animals. In one PPF/MMA treated case, there was complete sterilization of the infected site. In all cases, where debridement was performed, there was at least 2 to 3 orders of magnitude fewer organisms cultured from PPF/MMA animals than from PMMA treated animals. Control animals demonstrated 1 to 6 orders of magnitude more bacteria by quantitative culture than did treated animals.

While the composition of the present invention has been described for use as a medication-bearing composition for the controlled delivery of medication in vivo as well as for use as a surgical cement for prosthetic appliances, such descriptions are illustrative only and are not intended to be limiting in any way. There are many other applications for the biodegradable composites of the present invention. For example, the surgical cement of the present invention could be used for the repair of osteoporotic fractures. Such fractures are difficult and often not possible to treat by conventional internal fixation methods using bone plates and screws because the bone screws are prone to loosen or to cut through the weaker osteoporotic bone. Although some surgeons use conventional PMMA bone cement to secure the bone screws, there is a risk that PMMA will actually impair the healing process. Any such impairment is detrimental because if the bone fragments do not heal, the fixation eventually will fail.

Moreover, osteoporosis-induced fractures frequently involve a crushing-type injury by which porous bone collapses into itself typically causing a large void or bony defect at the site of the fracture. In order to achieve secure stabilization of the fracture, this bony defect must be filled in. Conventional surgical techniques employ the use of a bone graft from another site in the body to pack and fill the cavity. The bone graft consolidates as living bone slowly grows into the graft. Patients with such fractures in the lower extremities must remain non-weight-bearing for periods of up to three months because the bone grafts are too weak to provide sufficient structural support. Hospitalization, nursing home care, traction, and medical complications associated with immobilization are, of course, very expensive and problematic for the patient. The use of a biodegradable bone cement would alleviate the problems caused by prolonged, non-weight-bearing immobilization. A bone cavity could simply be filled with the biodegradable cement of the present invention, which would quickly set-up to form a strong solid mass. Patients could begin full weight-bearing activities within several days after the operation. The advantages are obvious in that the patient would experience a much shorter hospitalization period. Over time, the biodegradable bone cement would slowly resorb as the fracture healed and the cement could be replaced by living bone.

In addition, the surgical cement of the present invention can also be employed advantageously in the treatment of bone tumors. Such treatment typically involves excision of the tumor as well as portions of the surrounding bone, leaving a large cavity in the bone. An autogenous bone graft, or bone harvested from another site in the patient's body, is the conventional and accepted technique for filling such bony defects. While experimental clinical tests show that autogenous bone provides the most rapid incorporation of new bony ingrowth into a bone cavity, a disadvantage is that associated with the morbidity caused by the required surgical exposure for harvesting of the patient's bone. Moreover, some patients, particularly osteoporotic individuals, have very limited amounts of bone that are appropriate for use as a graft. Alternatively, allographs, i.e., bones taken from other individuals, may be used as bone-grafting material. There are certain risks associated with such allographs, however, including the transfer of infections and even unrecognized malignant cells from the harvested patient to the grafted patient as well as the problem of immunologic barriers between all individuals. Furthermore, such processes are complicated and labor-intensive.

For these reasons, some surgeons have begun to employ synthetic bone substitutes. The two most common types of substitutes are hydroxyappatite (HA) and tricalcium phosphate (TCP). HA and TCP have bioactive surfaces that promote osteoconduction when implanted in a bone cavity. In addition, TCP has the property of being slowly resorbed by the host tissues. A biodegradable surgical cement would have important advantages over conventional bone substitutes such as TCP and HA particulates because the cement could be injected and molded to fill a cavity of any shape and would harden sufficiently to immediately allow weight-bearing activities. Moreover, unlike man-made materials, the problems with procurement, infection, and storage would be obviated.

While we have described the invention with respect to specific materials, operating conditions, and procedures, such are illustrative only. Numerous modifications and equivalents will be apparent to those of ordinary skill in this art without departing from the spirit of the invention.

What is claimed is:

1. A composition comprising a particulate biocompatible resorbably calcium salt and a sintered particulate calcium phosphate ceramic dispersed in a polymer matrix formed by cross-linking a biodegradable polyester of fumaric acid and a polyhydric $C_2$-$C_6$ alcohol with methyl methacrylate, said polyester having a number average molecular weight of about 500 to about 1200.

2. The composition of claim 1 wherein the biodegradable polyester is a polyester of fumaric acid and propylene glycol.

3. The composition of claim 2 wherein the particulate calcium phosphate ceramic is selected from the group consisting of tricalcium phosphate, hydroxyapatite, and combinations thereof.

4. The composition of claim 3 wherein the particulate calcium phosphate ceramic is tricalcium phosphate.

5. The composition of claim 2 wherein the calcium salt is selected from the group consisting of calcium carbonate, calcium sulfate, precipitated calcium phosphate, calcium sulfate hemihydrate and combinations thereof.

6. The composition of claim 2 wherein the weight ratio of particulate calcium phosphate ceramic to particulate resorbable calcium salt ranges from about 1:4 to about 4:1.

7. The composition of claim 6 wherein the particulate calcium phosphate ceramic has an average particle diameter of about 75 microns to about 600 microns and the particulate resorbable calcium salt has a particle diameter of less than 10 microns.

8. The composition of claim 7 wherein the weight ratio of particulate calcium phosphate ceramic to particulate resorbable calcium salt is about 1:1.

9. The composition of claim 8 wherein the cross-linked biodegradable polyester matrix comprises poly)-propylene glycol fumarate) cross-linked using about 5% to about 20% by weight of methyl methacrylate monomer.

10. The composition of claim 1 wherein the polyhydric $C_2$-$C_6$ alcohol is selected from the group consisting of ethylene glycol, 1,2-propylene glycol, 1,3-propylene glycol, glycerine, 1,3-butanediol, 1,2-butanediol, 4-methyl-1,2-butanediol, 2-methyl-1,3-propanediol, and 4-methyl-1,2-pentanediol.

11. The composition of claim 2 wherein about 15 weight percent methyl methacrylate is used to cross-link the poly(propylene glycol fumarate).

12. The composition of claim 2 wherein the weight ratio of particulates to polyester matrix ranges from about 5:1 to about 1:2.

13. The composition of claim 12 wherein the weight ratio of particulates to polyester matrix is about 2:1.

14. The composition of claim 12 wherein the particulate, biocompatible resorbable calcium salts are selected from the group consisting of calcium carbonate, calcium sulfate, calcium sulfate hemihydrate, precipitated calcium phosphate, and combinations thereof.

15. A kit for preparing a biodegradable surgical cement comprising a sintered particulate calcium phosphate ceramic and a resorbable calcium salt selected from the group consisting of calcium carbonate, calcium sulfate and calcium sulfate hemihydrate, poly(propylene glycol fumarate) having a number average molecular weight of about 500 to about 1200, and methyl methacrylate for cross-linking the poly(propylene glycol fumarate).

16. The kit of claim 15 containing:
- a tricalcium phosphate ceramic and a calcium salt selected from the group consisting of calcium carbonate and calcium sulfate hemihydrate, the weight ratio of tricalcium phosphate ceramic to the calcium salt being about 2:1 to about 1:2;
- poly(propylene glycol fumarate) having a number average molecular weight of about 500 to about 1200; and
- a chemical cross-linking means comprising methyl methacrylate and a free-radical initiator, the weight ratio of the calcium salts and calcium phosphate ceramics to the total weight of polyester and chemical cross-linking means being about 2:1, said poly(propylene glycol fumarate) and said methyl methacrylate being in a weight ratio of about 4:1 to about 9:1, respectively.

* * * * *